(12) United States Patent
Vukmirovic et al.

(10) Patent No.: US 8,648,175 B2
(45) Date of Patent: *Feb. 11, 2014

(54) STABLE PHARMACEUTICAL COMPOSITION COMPRISING ERYTHROPOIETIN

(75) Inventors: Andreja Vukmirovic, Ljubljana (SI); Tanja Rozman Peterka, Celje (SI); Jelka Svetek, Ljubljana (SI); Alenka Paris, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 1479 days.

This patent is subject to a terminal disclaimer.

(21) Appl. No.: 10/521,296

(22) PCT Filed: Nov. 8, 2002

(86) PCT No.: PCT/IB02/04690

§ 371 (c)(1), (2), (4) Date: May 24, 2005

(87) PCT Pub. No.: WO2004/006948

PCT Pub. Date: Jan. 22, 2004

(65) Prior Publication Data

US 2005/0238720 A1 Oct. 27, 2005

(30) Foreign Application Priority Data

Jul. 17, 2002 (SI) .................. P-200200176

(51) Int. Cl.
*C07K 16/00* (2006.01)

(52) U.S. Cl.
USPC .............. 530/388.23; 424/1.41; 435/335; 514/970

(58) Field of Classification Search
None
See application file for complete search history.

(56) References Cited

U.S. PATENT DOCUMENTS 4,647,454 A 3/1987 Cymbalista
4,992,419 A * 2/1991 Woog et al. .............. 514/8

FOREIGN PATENT DOCUMENTS

EP 0 528 314 2/1993
EP 0 909 564 4/1999
EP 909564 A1 * 4/1999

OTHER PUBLICATIONS

Mastanduono et al., Treating Anemia Associated with Chemotherapy, [online], Retrieved Oct. 7, 2008, Retrieved from URL:<http://www.uspharmacist.com/oldformat.asp?url=newlook/files/feat/acf2fd7.htm>.*
Kollidon 12 PF, [online], Phara ingredients & Services, Retrieved Oct. 7, 2008, Retrieved from URL:<www.Basf.com>.*
Wang et al., "Parenteral Formulations of Proteins and Peptides: Stability and Stabilizers", Journal of Parenteral Science and Technology, vol. 42, No. 2S, pp. S04-S26 (1988).

* cited by examiner

*Primary Examiner* — Lezah Roberts
*Assistant Examiner* — Nannette Holloman
(74) *Attorney, Agent, or Firm* — Luedeka Neely Group, P.C.

(57) ABSTRACT

The present invention provides a new stable pharmaceutical composition of erythropoietin (EPO) that is stabilized with PVP.

16 Claims, 7 Drawing Sheets

STABLE PHARMACEUTICAL COMPOSITION COMPRISING ERYTHROPOIETIN

FIELD OF THE INVENTION

The present invention relates to a new stable pharmaceutical composition which comprises erythropoietin (EPO).

EPO is a glycoprotein hormone which regulates the formation of erythrocytes in mammals. It acts as growth and/or differential factor to the erythroid progenitor cells in bone marrow and causes their proliferation and differentiation to erythrocytes.

BACKGROUND OF THE INVENTION

Naturally occurring human EPO is produced by the kidney and is the humoral plasma factor which stimulates red blood cell production. It stimulates the division and differentiation of committed erythroid progenitors in the bone marrow. (Goldwasseret et al., *J. Biol. Chem.*, 249, 4202-4211, 1974, Sherwoodet et al., *Endocrinology*, 103, 866-870, 1978). It is produced in adult kidneys (Sherwood et al., Endocrinology, 103, 866-870, 1978) and in fetal liver (Zanjani et Al., J. Lab. Clin. Med., 89, 640-644, 1977).

The administration of a pharmaceutical composition of EPO to the organism stimulates and/or accelerates the production of erythrocytes. The pharmaceutical composition of EPO is used in the treatment of chronic renal failure, anemia secondary to chemotherapy treatment in cancer and anemia associated with zidovudine treatment of human immunodeficiency virus infection and in the treatment of other kinds of anemias (Danna et al., Erythropoietin in Clinical Applications—An International Perspective. New York, N.Y.: Marcel Dekker; 301-324, 1990; Eschbach in sod., *N. England J. of Med.*, 316, 2, 73-78, 1987; Krane, *Henry Ford Hosp. Med. J.*, 31,3, 177-181, 1983).

Recombinant EPO, which is the product of expression of the human EPO gene in mammalian cells is used in pharmaceutical compositions of EPO (EP 148605, EP 205564, EP255231). Also some EPO analogs and derivatives are described in the art: EP640619, EP 668351, WO 9412650, EP1064951, WO 0232957, WO 9533057, U.S. Pat. No. 5,916,773, WO 09902710, U.S. Pat. No. 5,580,853, U.S. Pat. No. 5,747,446, U.S. Pat. No. 5,919,758 and U.S. Pat. No. 6,107,272.

Pharmaceutical compositions of EPO, which comprise human serum albumin, are described in: EP 178665, EP 178576, U.S. Pat. No. 5,661,125, WO 0061169. Human serum albumin can cause allergic reactions (Stafford C T et al., *Ann Allergy*, 61(2), 85-88, 1988). Furthermore there exist a risk of infection with viruses when a pharmaceutical composition comprises human blood products. Therefore pharmaceutical formulations of EPO that are stable and are free of human blood products, such as albumin are needed.

EP 306824, EP 607156, EP 528313 and EP 528314 describe pharmaceutical compositions, in which urea is used as an EPO stabilising agent.

EP306824, EP 178665, GB 2171304, EP 528314, EP 528313 and EP 1002547 describe lyophilized formulations of EPO.

U.S. Pat. No. 5,376,632 describes a pharmaceutical formulations, in which alpha and beta cyclodextrines are used.

EP 607156, EP 528313 in EP178665 describe aqueous pharmaceutical compositions of EPO, which comprise antimicrobial preservatives such as benzyl alcohol, parabens, phenols, and mixtures thereof.

EP 909564, EP 528314, EP 430200 and WO 0061169 describe the use of aminoacids and/or the combination of aminoacids and non-ionic detergents as stabilising agents.

WO 0187329 describes different pharmaceutical compositions of pegylated EPO analog. The described pharmaceutical compositions are essentially based on the use of sulfate buffer.

Pharmaceutical compositions of EPO described in: RU 2128517, WO0061169, EP 528313, EP 607156, EP 528314, EP 178665, are prepared in citrate buffer.

SUMMARY OF THE INVENTION

The object of the invention is to provide a pharmaceutical composition comprising EPO which is capable of beneficially stabilising EPO.

The present invention provides a new stable pharmaceutical composition comprising EPO, a pharmaceutically acceptable pH buffering system, and polyvinylpyrrolidone (PVP). The present invention also provides a use of PVP for the stabilization of erythropoietin (EPO) in an aqueous solution, a process for preparing a composition containing erythropoietin (EPO), comprising mixing EPO with PVP, and a use of a composition comprising EPO, a pharmaceutically acceptable pH buffering system, and polyvinylpyrrolidone (PVP for the treatment and/or prevention of diseases indicated for erythropoietin (EPO).

The pharmaceutical composition is formulated with a pharmaceutically acceptable pH buffering system and with povidone (polyvinylpyrrolidone; PVP) acting as a stabilising agent. The stabilisation of EPO is achieved while the composition of the invention is preferably free of additives which are derived from human or animal origin other than EPO (e.g. serum proteins). The pharmaceutical composition optionally further comprises an isotonifying agent and/or one or more pharmaceutically acceptable excipients. The pharmaceutical composition of the present invention is suitable for use in human and veterinary medicine and is pharmaceutically acceptable in a suitable administration form, especially for parenteral application, e.g. intramuscular, subcutaneous and/or intravenous application. In a particularly preferred embodiment, the pharmaceutical composition of the present invention is in a liquid, more preferably in an aqueous form.

DESCRIPTION OF THE INVENTION AND OF PREFERRED EMBODIMENTS

Figure 1:
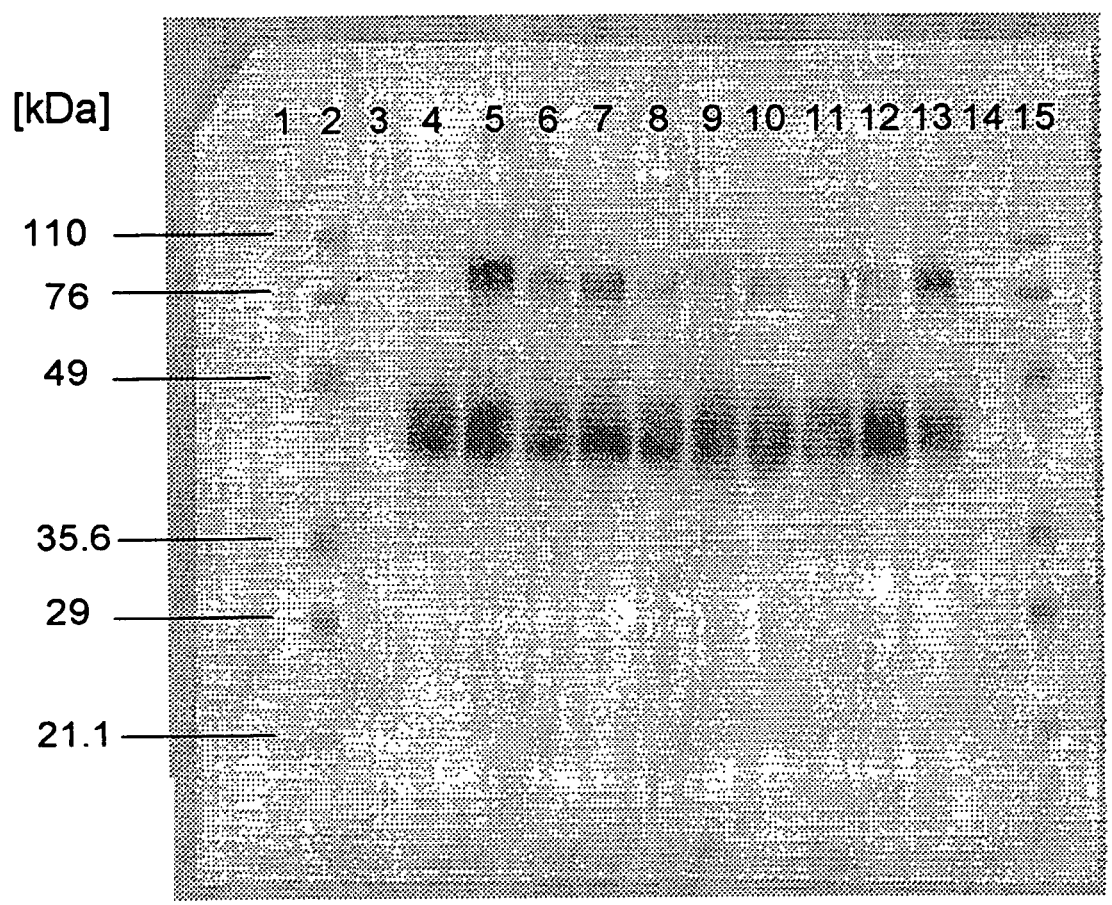
FIG. 1 shows SDS-PAGE analysis of inventive and reference samples comprising EPO after having been stored at 40° C. (±2° C.) for 1 month.

It was surprisingly found that a pharmaceutical composition which comprises PVP, and which is preferably free of additives other than EPO derived from human and/or animal origin, beneficially stabilises EPO.

The present invention provides the pharmaceutical composition of EPO comprising:
  a. a therapeutically effective amount of EPO,
  b. a pharmaceutically acceptable pH buffering system, and
  c. PVP.

The present invention also provides the pharmaceutical composition of EPO which optionally further comprises in addition to components a-c:
  d. an isotonifying agent and/or
  e. one or more of other pharmaceutically acceptable excipients.

The composition of the invention is preferably free of additives derived from human or animal origin.

The term 'erythropoietin (EPO)' refers to a protein with the in vivo biological activity of causing bone marrow cells to increase production of reticulocytes and red blood cells and is selected from the group consisting of human EPO and derivatives and analogs which are defined below.

The term 'therapeutically effective amount of EPO' refers to the amount of EPO which enables a therapeutical effect of EPO.

The term 'stabiliser' refers to a pharmaceutical acceptable excipient, which has a stabilising effect on EPO.

The term 'EPO stability' refers to the maintenance of EPO content and to the maintenance of EPO biological activity. The EPO stability may be influenced inter alia by the following processes: adsorption of EPO to the container walls, denaturation or degradation of EPO and aggregate formation of e.g. EPO dimers and/or EPO multimers and/or similar molecules with higher molecular weight. These processes occur due to exposing of the samples to different conditions, e.g. higher temperature, inappropriate containers, use of wrong stabilisers of EPO, sunshine, inappropriate way of storing and/or inappropriate isolation procedure.

The term "free of additives derived from human and/or animal origin" refers to the condition that additives which originate from human and/or animal and which are different from EPO, such as serum albumins like HSA or BSA, are not intentionally added to the composition, or if originally present in an EPO preparation have been separated or reduced during the purification and/or isolation of EPO to an unavoidable level of traces, preferably to a level that is typically undetectable by standard analytical methods.

It has been surprisingly found that formulating EPO in the composition of the invention improves its stability at temperatures above refrigerator temperature (e.g. 2-8° C.), especially at room temperature (i.e. below 25° C.) and even at higher temperatures (e.g. 40° C.). This means that the composition can be stored without cooling for a prolonged period of time (more than 10 weeks at room temperature), without loosing significant amounts of activity and without significant degradation.

In the pharmaceutical composition of the present invention, besides the pH buffering system and optionally besides an isotonifying agent and/or a further pharmaceutically acceptable excipient PVP alone may be used as the effective EPO stabiliser and no further stabilisers are necessary for stabilising EPO. PVP can therefore replace the combinations of different stabilisers which are known to be used to maintain the EPO stability in pharmaceutical compositions of EPO described in the prior art. The preparation of a pharmaceutical composition which comprises only one effective stabiliser instead of two or more stabilisers is better from the economical viewpoint. The preparation is more easily performed, the expenses are lower, the preparation is less time consuming and the patient receives less additives in the organism. Although not being restricted in this way, the pharmaceutical composition of the present invention may therefore preferably consist only of the aforementioned constituents a.-c., or optionally a.-d., a.-c. plus e. or a.-e.

In some pharmaceutical compositions known from the prior art the non-ionic detergents like Polysorbate 80 are used as stabilisers of EPO. The use of PVP is advantageous over the use of polysorbates because gel filtration can be used as analytical method for the determination of EPO dimers, EPO multimers and related substances with higher molecular mass which result from the aggregation of EPO molecules. The polysorbates are eluted at the same time as EPO dimers do. Therefore the gel filtration can not be used as a detection method for EPO dimers for the pharmaceutical compositions which comprise polysorbates. The use of PVP therefore contributes to an easier way of proving of EPO stability, to an increased safety and an easier control of the quality of pharmaceutical composition of EPO.

The pharmaceutical composition of the present invention is preferably a liquid and particularly an aqueous pharmaceutical composition. Such a liquid composition can be directly used for parenteral application such as subcutaneous, intravenous or intramuscular application without reconstitution, diluting or additional preparation steps which could lead to a lowering or even a loss of EPO biological activity, and also can contribute to avoid additional technical problems occurring at the time of application. The use of a liquid pharmaceutical composition is therefore more practical as the use of lyophilized formulations. Liquid and particularly aqueous formulations of EPO are generally preferred over lyophilized formulation for preparing the clinical formulation of EPO, because the reconstitution process of lyophilized compositions is time consuming, poses risks of improper handling of the protein formulation, or may be reconstituted improperly, and certain additives such as stabilisers are usually required to retain sufficient activity of the drug.

The pharmaceutical composition of the present invention is most preferably free of additives derived from human or animal origin like human serum proteins which, despite blood screening, pose a risk of infection with a transmissible agent. Further, although recombinant EPO is generally well tolerated, occasional skin rashes and urticaria have been observed suggesting allergic hypersensitivity to some components of the EPO formulation, likely human serum albumin.

The pharmaceutical composition of the present invention can be suitably prepared in isotonic solution and is expected to be pharmaceutically acceptable and causing no side effects like allergic hypersensitivity.

The pharmaceutical composition of the present invention can be used for all forms of EPO, comprising EPO alfa, EPO beta, EPO omega and other EPO preparations having different isoform profiles, as well as for specific EPO isoforms, EPO muteins, EPO fragments, EPO analogs such as EPO dimers, NESP (hyperglycosilated analog of recombinant human EPO), gene activated EPO, pegylated EPO, hybrid molecules with EPO, EPO fragments, fusion protein (oligomers and multimers) with EPO, EPO with modified glycosilation profiles regardless of the biological activity of EPO and further regardless of the method of synthesis or manufacture thereof, which method may include but is not limited to the isolation of naturally occurring EPO and recombinant EPO whether produced from cDNA or genomic DNA, synthetic, transgenic and gene activated methods.

The pharmaceutical composition of the present invention may comprise from 500 to 100000 units or more EPO per dose (1 IU corresponds to about 10 nanograms of recombinant EPO), preferably from 1000 to 40000 IU per dose. In general it is contemplated that an effective amount will be from 1 to 500 IU/kg body weight and more preferably from 50 to 300 IU/kg body weight, especially when EPO is given subcoutaneously. The effective amount will further depend on the species and size of the subject being treated, the particular condition or disease being treated and its severity and the route of administration. In preferred embodiments, the pharmaceutical quantity is formulated to provide a quantity per dose selected from the group consisting of about 1000 IU, about 2000 IU, about 3000 IU, about 4000 IU, about 10000 IU, about 20000 IU, about 25000 IU and about 40000 IU.

The pharmaceutical composition of the present invention can be filled in ampoules, injection syringes and vials. These enable the application in volumes in the suitable range from 0.2 to 20 ml per dose.

The preferred pH range for the solutions is from about 6 and to about 8 with a range from about 6.8 to about 7.5 being more preferred and a pH of about 7.0 being most preferred. The use of a phosphate buffer system, especially sodium phosphate dibasic and sodium phosphate monobasic such as $NaH_2PO_4 \times 2H_2O/Na_2HPO_4 \times 2H_2O$, is preferred. Other suitable buffer systems to maintain the desired pH range of about 6 to about 8 include, but are not limited to, sodium citrate/citric acid, sodium acetate/acetic acid, and any other pharmaceutically acceptable pH buffering agent known in the art. Citrate buffer may cause pain at the injection site. Therefore the phosphate buffer is more preferable for the parenteral application.

The concentration of buffering system, especially the phosphate buffer, depends on the desired pH of the formulation. The preferred concentration is in the range from 10 to 50 mM, more preferred from 15 to 35 mM, most preferred from 15 to 25 mM. There may be added a pH-adjusting agent such as, but not limited to HCl, NaOH, citric acid or sodium citrate.

The pharmaceutical composition of the present invention comprises PVP as an EPO stabiliser. In the meaning of the present invention, PVP is represented by the normal form of poly[1-(2-oxo-1-pyrrolidinyl)ethylen] also known as povidone or polyvinylpyrrolidone. The use of low molecular weight PVP, in particular PVP K12 to K18, is preferred, and the use of PVP K12 is most preferred. The content of PVP in the composition of the invention should provide a stabilising effect on EPO, suitably in an amount of at least 0.001% (w/v). The concentration of PVP is preferably in the range from about 0.01% to about 5.0%, more preferably from 0.1 to 1.0%, most preferred at about 0.5% (w/v).

The pharmaceutical composition of the present invention optionally further comprises an agent capable of rendering the formulations of the present invention isoosmotic with human blood. Typical suitable isotonifying agents are well known in the art, and include, but are not limited to, agents selected from the group consisting of inorganic salts such as NaCl, $CaCl_2$, mannitol, glycine, glucose and sorbitol. Use of NaCl as an isotonifying agent is preferred in the formulations of the present invention.

Although the formulation with PVP as the sole effective stabiliser is preferred as mentioned above, the pharmaceutical composition of the present invention may optionally comprise more than one type of stabiliser besides the aforementioned components a., b. and optionally d. and e., if desired. This additional stabiliser is preferably selected from the group which comprises surfactants such as sorbitane derivates/polysorbates such as e.g. polysorbate 20, polysorbate 80, and poloxameres such as Pluronic 68. Among them, Pluronic F68 is particularly preferred and is suitably used in the concentration at about 1% or less than 1%, more preferably in the concentration of 0.05 to 0.2%.

The pharmaceutical composition of the present invention may optionally further comprise one or more pharmaceutically acceptable excipients. Suitable pharmaceutically acceptable excipients include polyols selected from the group of mannitol, sorbitol, glycerol and polyethylenglycol, hydroxypropylcellulose, methylcellulose, macrogol esters and ethers, glycol and glycerol esters, amino acids such as glycine, L-isoleucine, L-leucine, L-glutamic acid, L-2-phenylalanine, L-threonin.

The composition of the present invention can be used for the preparation of medicaments for the treatment and/or prevention of diseases that are indicated for EPO. Examples of medical uses include a variety of therapies where stimulation of red blood cell proliferation (RBC) is desired, where there exists an endogenous hormone deficiency, where blood is lost or where a patient has indications of anemia, or has hyporesponsiveness of the bone marrow to the endogenous hormone. These medical indications are for example anemia of malignant disease (i.e. any type of solid cancer, or hematological cancer including leukemia, lymphoma and multiple myeloma), anemia resulting from a chemotherapeutic/radiation treatment of a malignant disease, anemia of chronic disease including for example autoimmune diseases such as rheumatoid arthritis and hepatitis, anemia in AIDS patients, especially those treated with AZT, anemia of prematurity, anemia associated with (chronic) renal failure, anemia of thalasemia, autoimmune hemolytic anemia, aplastic anemia, and anemia associated with surgery (e.g. for improving preoperative blood donation for autotransfusion to stimulate and increase in hemoglobin levels to counter substantial blood loss or to increase erythropoiesis in subjects undergoing bone marrow transplantation), the treatment of fatigue, pain, chronic heart failure, dysrythmia or dementia, preoperatively use to reduce the need for allogenic blood transfusion in non-vascular and non-cardiac surgery and other indications indicated for EPO.

The following examples illustrate the present invention without, however, limiting the same thereto.

EXAMPLES

Analytical Methods

The following analytical methods were used for the analysis of the pharmaceutical composition of the present invention: SDS-PAGE with immunodetection, size exclusion chromatography (SEC), EPO-ELISA and in vivo biological activity assay on mice.

SDS-PAGE with immunodetection: The loading samples were prepared in the loading buffer free of reducing agent. The vertical SDS-PAGE was used: gel NuPAGE Bis-Tris 12%, 8×8 cm, thickness 1.0 mm, 15 lanes (Invitrogen) in MOPS SDS electrophoresis buffer (Invitrogen). Electrophoresis ran 1 hour at constant voltage of 200 V. After the electro transfer from the gel to the nitro-cellulose membrane the immunodetection was performed in two steps. In the first one the primary antibodies (anti-huEPO, mouse, monoclonal) were used. In the second step the secondary antibodies (anti-mouse IgG, rabbit, polyclonal) conjugated to horseradish peroxidase was used. The addition of the peroxidase substrate triggers enzyme reaction to form a blue coloured complex.

EPO-ELISA: System EPO-ELISA Quantikine IVD, R&D Systems, is based on the double-antibody sandwich method. Microplate wells, precoated with monoclonal (murine) antibody specific for EPO are incubated with specimen or standard. EPO binds to the immobilized antibody on the plate. After removing specimen or standard, wells are incubated with an anti-EPO polyclonal (rabbit) antibody conjugated to horseradish peroxidase. During the second incubation, the antibody-enzyme conjugate binds to the immobilized EPO. A chromogen is added to the wells and is oxidized by the enzyme reaction to form a blue coloured complex. The amount of colour generated is directly proportional to the amount of conjugate bound to the EPO antibody complex, which, in turn, is directly proportional to the amount of EPO in the specimen or standard.

SEC: SEC was used to determine the proportion of EPO dimers and related substances of higher molecular mass in the samples from FP1 to FP8 with the EPO content from 2000 IU/ml to 10000 IU/ml. The limit assay following the protocols of European Pharmacopoeia was used (European Pharmacopoeia 2002, 4$^{th}$ edition, Erythropoietin concentrated solution).

In Vivo Biological Activity:

The protocol for in vivo determination of biological activity on hypoxic mice described in Eur. Ph was used. The estimation of biologic activity was performed under the protocols from Eur. Ph as well (Eur. Pharmacopoeia—1997; Statistical Analysis of Results of Biological Assays and Tests; The parallel-line model). Under the demands of Eur. Ph the estimated value of biologic activity should be in the range between 80% and 120% of the marked activity. The aim of the method is to reach the range between 80% and 120% regarding the content (value) of the EPO injected (10000 IU/ml) and the results obtained represent the estimation of biological activity and not its precise value. The confidential limit should be in the range between 64% and 156% of the marked activity.

The Conditions for Testing the Stability of Pharmaceutical Compositions of EPO

| HL-reference | 2 to 8° C., refrigerator |
| 40 | 40° C. ± 2° C., 75% ± 5% relative humidity, climatic chamber |
| 25 | 25° C. ± 2° C., 60% ± 5% relative humidity, climatic chamber |

Example 1

Stability Tests

The following compositions of the formulations FP1 through FP8 were prepared:

FP1: polysorbate 80 (0.03%. (weight/volume (w/v))), glycine (0.5% (w/v)), phosphate buffer 20 (mmol/l), NaCl (100 mmol/l)

FP2: glycine (0.5% (w/v)), glycerol (1.4% (w/v)), phosphate buffer (32 mmol/l)

FP2: glycine (0.5% (w/v)), Pluronic F68 (0.1% (w/v)), phosphate buffer (20 mmol/l), NaCl (90.6 mmol/l)

FP4: sorbitol (4.5% (w/v)), Pluronic F68 (0.1% (w/v)), phosphate buffer (20 mmol/l)

FP5: dextran 70 (1% (w/v)), NaCl (123 mmol/l), phosphate buffer (20 mmol/l)

FP6: glycerol (2% (w/v)), Pluronic F 68 (0.1% (w/v)), NaCI (17.1 mmol/l) phosphate buffer (20 mmol/l)

FP7: glycerol (2% (w/v)), PVP K12 (0.5% (w/v)), phosphate buffer (20 mmol/l).

FP8: PVP K12 (0.5% (w/v)), NaCl (123 mmol/l), phosphate buffer (20 mmol/l)

The content of EPO in the formulations is set to 2000 IU/ml or 10000 IU/ml, as ribed below.

Samples from FP1 to FP8, with a respective EPO content of 10000 IU/ml, were stored at 40° C. (±2° C.) for 1 month (40). EPO bulk in phosphate buffer stored at 40° C. (±2° C.) for 1 month was taken as a positive control (PK) for the determination of the content of EPO dimers. The samples were subjected to SDS-PAGE; 0.4 μg was loaded in each lane. FIG. 1 shows the results.

Legend of FIG. 1:

| Lane | Sample |
| --- | --- |
| 1 | empty lane |
| 2 | prestained SDS-PAGE MW standards, low range, Bio-Rad, 4 μl load |
| 3 | empty lane |
| 4 | EPO-BRP (EPO standard of the European Pharmacopoeia) |
| 5 | FP 1 40 |
| 6 | FP2 40 |
| 7 | FP3 40 |
| 8 | FP4 40 |
| 9 | FP5 40 |
| 10 | FP6 40 |
| 11 | FP7 40 |
| 12 | FP8 40 |
| 13 | PK |
| 14 | empty lane |
| 15 | prestained SDS-PAGE MW standards, low range, Bio-Rad, 4 μl load |

Figure 2:
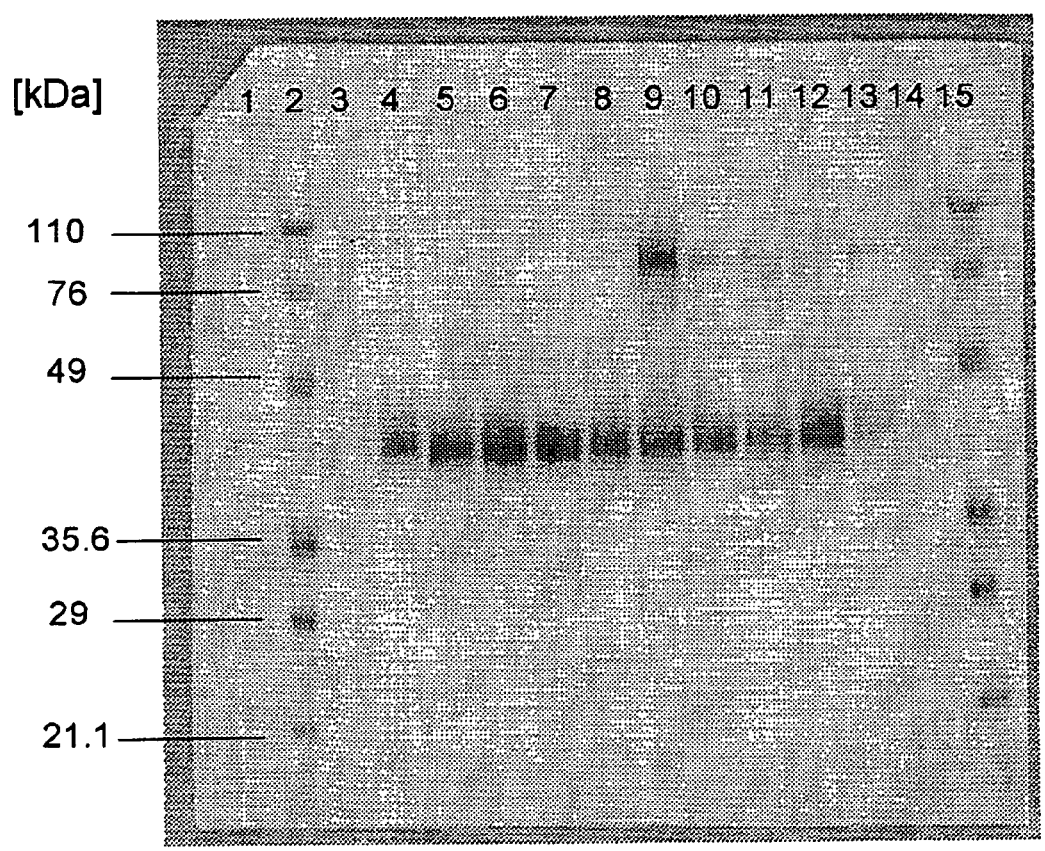
FIG. 2 shows SDS-PAGE analysis of reference samples comprising EPO when being stored in the refrigerator for 1 month in comparison with being stored at 40° C. (±2° C.) for 1 month.

FIG. 2 shows the SDS-PAGE of the samples from FP1 to FP4, with a respective EPO content of 10000 IU/ml, stored in the refrigerator (HL) and stored at 40° C. (±2° C.) 1 month (40). EPO bulk in phosphate buffer stored at 40° C. (±2° C.) 1 month was taken as a positive control (PK) for the determination of the content of EPO dimers. 0.4 μg was loaded in each lane.

Legend of FIG. 2:

| Lane | Sample |
| --- | --- |
| 1 | empty lane |
| 2 | prestained SDS-PAGE MW standards, low range, Bio-Rad, 4 μl load |
| 3 | empty lane |
| 4 | EPO-BRP (EPO standard of the European Pharmacopoeia) |
| 5 | FP 1 HL |
| 6 | FP2 HL |
| 7 | FP3 HL |
| 8 | FP4 HL |
| 9 | FP1 40 |
| 10 | FP2 40 |
| 11 | FP3 40 |
| 12 | FP4 40 |
| 13 | PK |
| 14 | empty lane |
| 15 | prestained SDS-PAGE MW standards, low range, Bio-Rad, 4 μl load |

Figure 3:
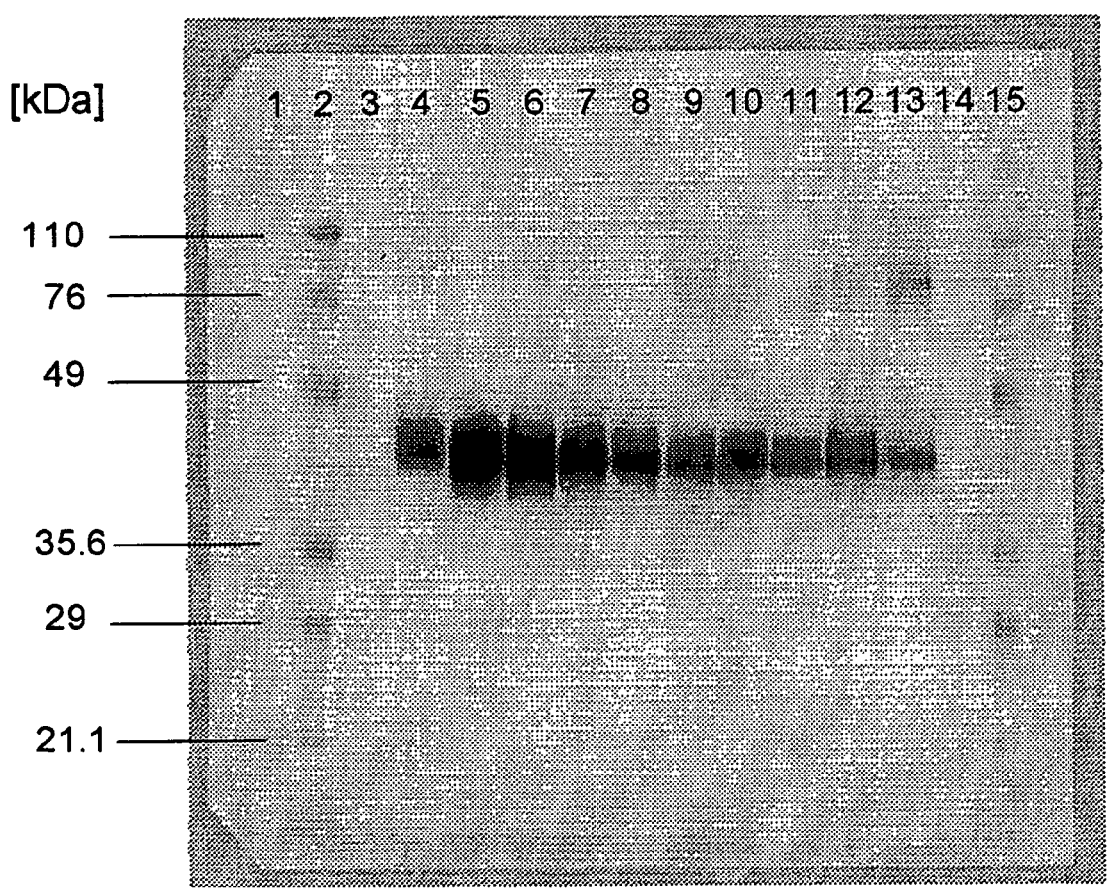
FIG. 3 shows SDS-PAGE analysis of the inventive and reference samples comprising EPO when being stored in the refrigerator for 1 month in comparison with being stored at 40° C. (±2° C.) for 1 month.

FIG. 3 shows the SDS-PAGE of the samples from FP5 to FP8, with a ective EPO content of 10000 IU/ml, stored in the refrigerator (HL) and stored at (40° C.) 1 month (40). EPO bulk in phosphate buffer stored at 40° C. (±2° C.) 1 month was taken as a positive control (PK) for the determination of the content of EPO dimers. 0.4 µg was loaded in each lane.

Legend of FIG. 3:

| Lane | Sample |
| --- | --- |
| 1 | empty lane |
| 2 | prestained SDS-PAGE MW standards, low range, Bio-Rad, 4 µl load |
| 3 | empty lane |
| 4 | EPO-BRP (EPO standard of the European Pharmacopoeia) |
| 5 | FP 5 HL |
| 6 | FP6 HL |
| 7 | FP7 HL |
| 8 | FP8 HL |
| 9 | FP5 40 |
| 10 | FP6 40 |
| 11 | FP7 40 |
| 12 | FP8 40 |
| 13 | PK |
| 14 | empty lane |
| 15 | prestained SDS-PAGE MW standards, low range, Bio-Rad, 4 µl load |

Figure 4:
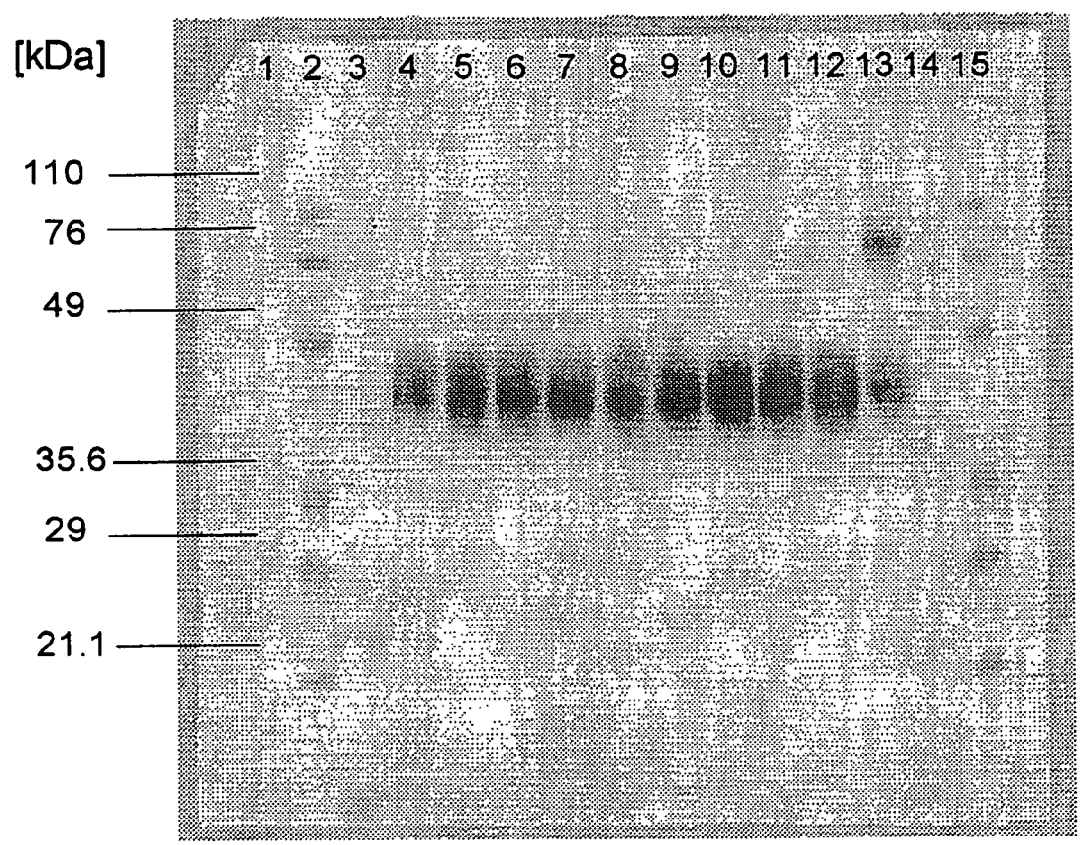
FIG. 4 shows an SDS-PAGE analysis of inventive and reference samples comprising EPO when stored in the refrigerator for 10 weeks.

FIG. 4 shows the SDS-PAGE of the samples from FP1 to FP8, with a respective EPO content of 10000 IU/ml, stored in the refrigerator (HL) 10 weeks. EPO bulk in phosphate buffer stored at 40° C. (±2° C.) 1 month was taken as a positive control (PK) for the determination of the content of EPO dimers. 0.4 µg was loaded in each lane.

Legend of FIG. 4:

| Lane | Sample |
| --- | --- |
| 1 | empty lane |
| 2 | prestained SDS-PAGE MW standards, low range, Bio-Rad, 4 µl load |
| 3 | empty lane |
| 4 | EPO-BRP (EPO standard of the European Pharmacopoeia) |
| 5 | FP1 HL |
| 6 | FP2 HL |
| 7 | FP3 HL |
| 8 | FP4 HL |
| 9 | FP5 HL |
| 10 | FP6 HL |
| 11 | FP7 HL |
| 12 | FP8 HL |
| 13 | PK |
| 14 | empty lane |
| 15 | prestained SDS-PAGE MW standards, low range, Bio-Rad, 4 µl load |

Figure 5:
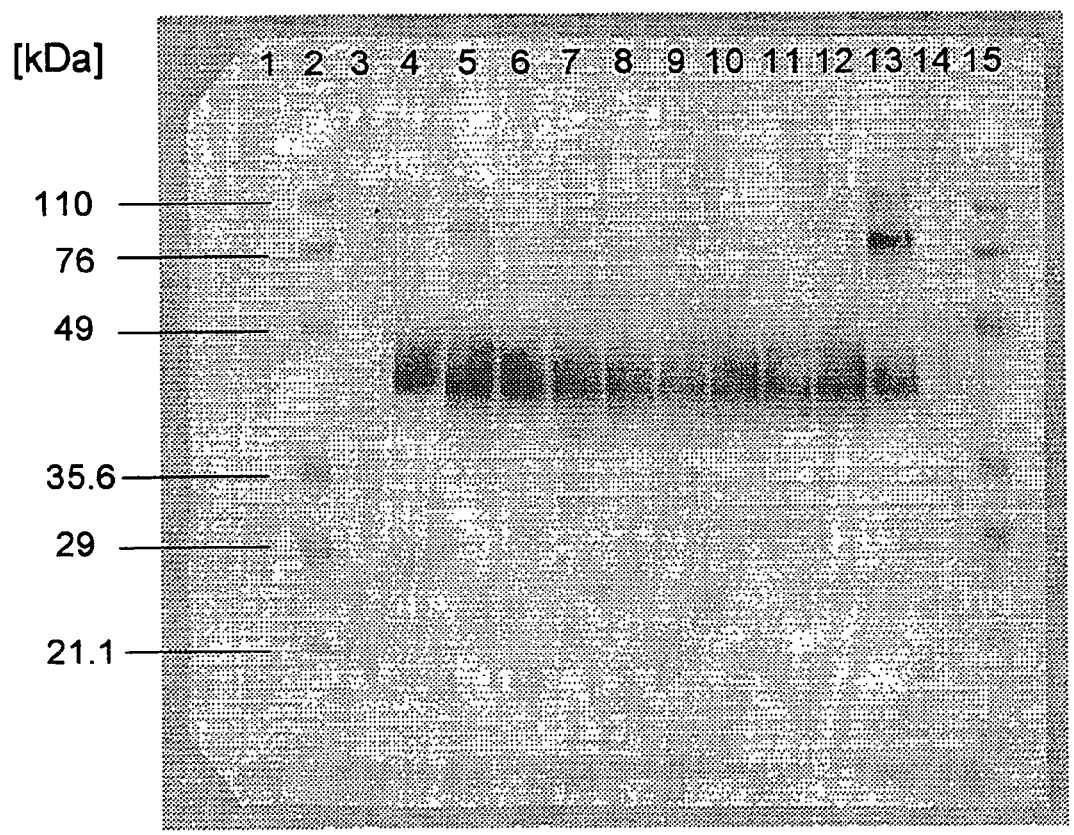
FIG. 5 shows an SDS-PAGE analysis of the inventive and reference samples comprising EPO when being stored at 25° C. (±2° C.) for 10 weeks.

FIG. 5 shows the SDS-PAGE of the samples from FP1 to FP8, with a respective EPO content of 10000 IU/ml, stored at 25° C. (±2° C.) 10 weeks (25). EPO bulk in phosphate buffer stored at 40° C. (±2° C.) 1 month was taken as a positive control (PK) for the determination of the content of EPO dimers. 0.4 µg was loaded in each lane.

Legend of FIG. 5:

| Lane | Sample |
| --- | --- |
| 1 | empty lane |
| 2 | prestained SDS-PAGE MW standards, low range, Bio-Rad, 4 µl load |
| 3 | empty lane |
| 4 | EPO-BRP (EPO standard of the European Pharmacopoeia) |
| 5 | FP1 25 |
| 6 | FP2 25 |
| 7 | FP3 25 |
| 8 | FP4 25 |
| 9 | FP5 25 |
| 10 | FP6 25 |
| 11 | FP7 25 |
| 12 | FP8 25 |
| 13 | PK |
| 14 | empty lane |
| 15 | prestained SDS-PAGE MW standards, low range, Bio-Rad, 4 µl load |

Figure 6:
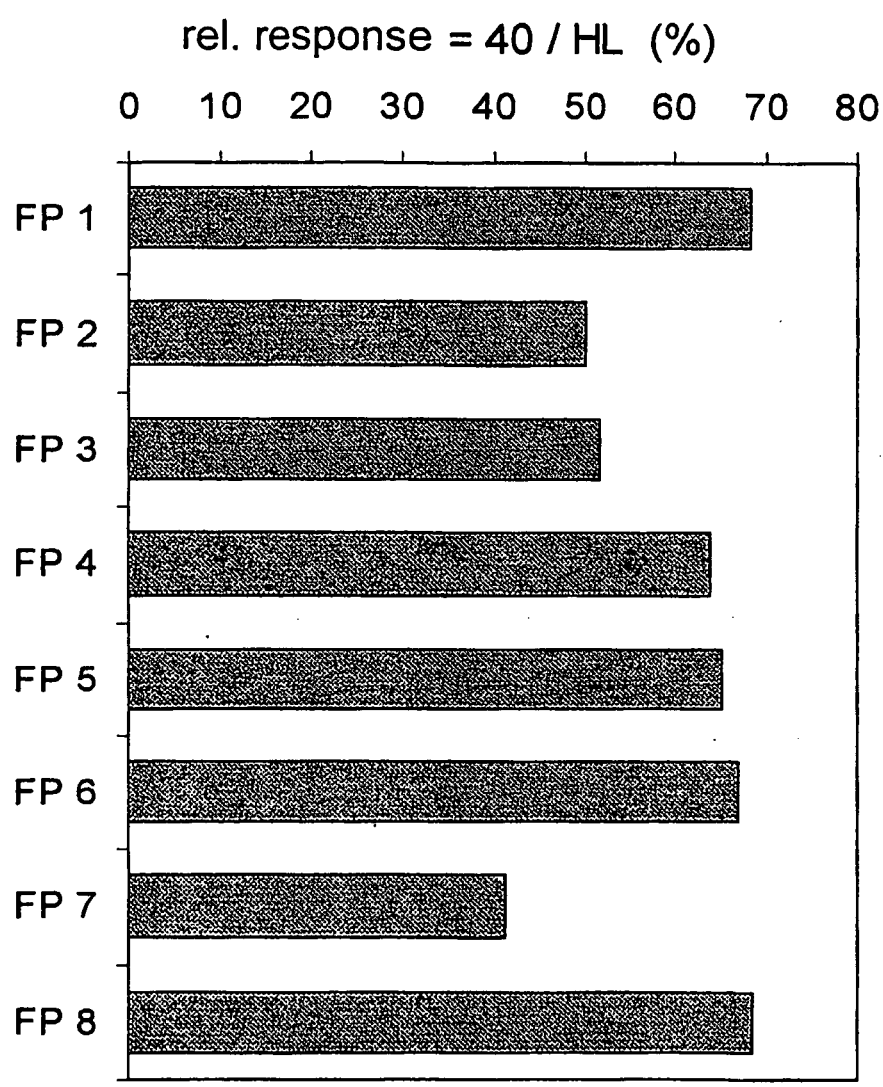
FIG. 6 shows the relative response EPO-ELISA (in %) of inventive and reference samples when stored at 40° C. (≅2° C.) for 1 month (40) to the respective samples when stored in the refrigerator for 1 month (HL).

FIG. 6 shows the relative response of EPO-ELISA (in %) of the samples from FP1 to FP8, with a respective EPO content of EPO 10000 IU/ml, stored at 40° C. (±2° C.) for 1 month (40), to the samples from FP1 to FP8, stored in the refrigerator for 1 month (HL).

Figure 7:
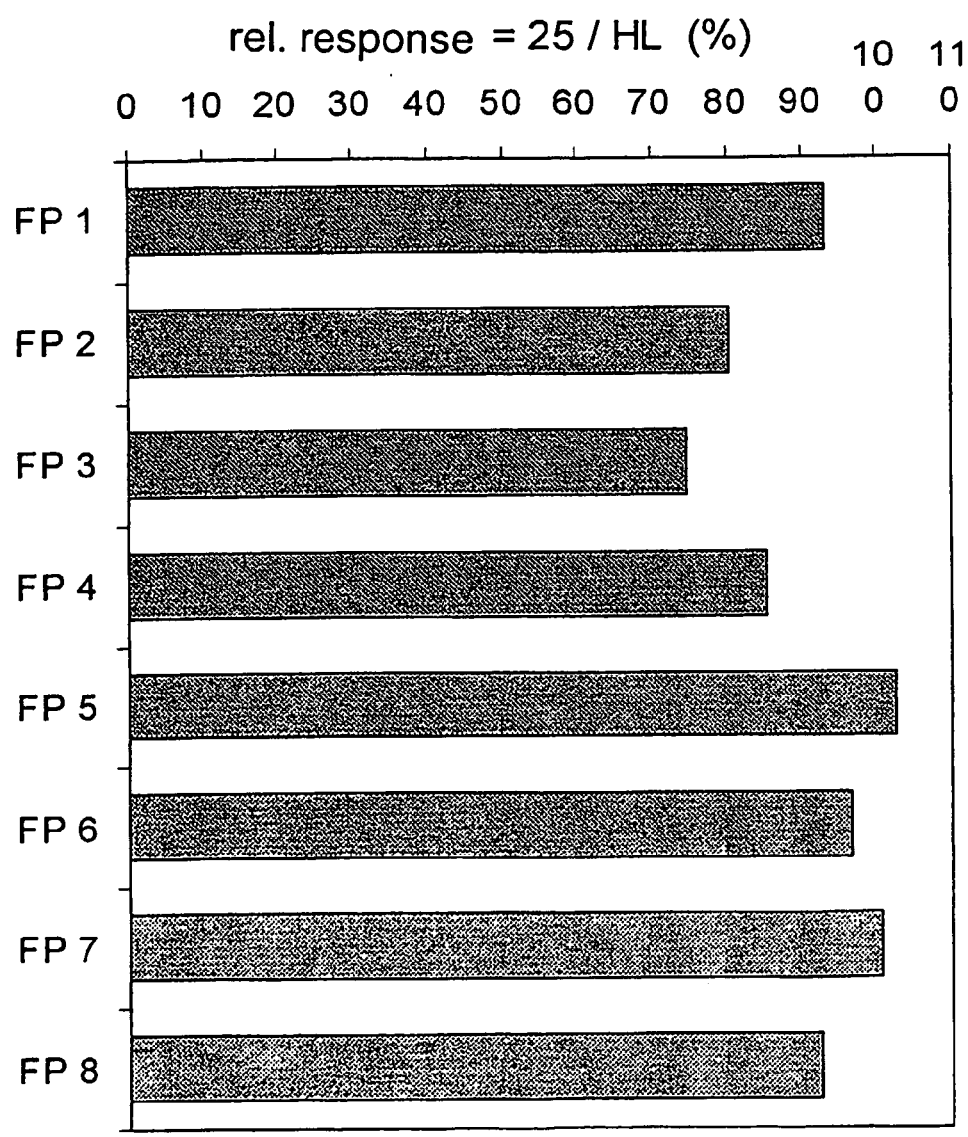
FIG. 7 shows the relative response EPO-ELISA (in %) of inventive and reference samples comprising EPO when stored at 25° C. (±2° C.) for 10 weeks (25) to the respective samples when stored in the refrigerator for 10 weeks (HL).

FIG. 7 shows the relative response of EPO-ELISA (in %) of the samples from FP1 to FP8, with a respective EPO content of EPO 10000 IU/ml, stored at 25° C. (±2° C.) for 10 weeks (25), to the samples from FP1 to FP8, stored in the refrigerator for 10 weeks (HL).

Results of Stability Tests:

The SDS-PAGE with immunodetection shows that EPO aggregates, for example EPO dimers and related substances of higher molecular mass, do not occur in the pharmaceutical composition of the present invention (FP7 and FP8) at room temperature (FIGS. 1-5). At elevated temperatures they are present in small amounts. Comparison of EPO stability at elevated temperature (1 month at 40° C.) of the pharmaceutical composition of the present invention with the pharmaceutical composition FP1, in which the combination of polysorbates and the amino acid glycine is used (FIGS. 1, 2, 3), shows that EPO dimers are formed in FP1. The formation of EPO dimers is one of crucial factors for EPO stability. It is also possible that EPO aggregates, e. g. EPO dimers and related substances of higher molecular mass measured, cause undesired side effects after the application and non-comfortability of the patient treated with the pharmaceutical composition. It is also possible that these aggregates cause immune response of the organism and the treatment with EPO has to be stopped.

The pharmaceutical composition of the present invention containing only PVP as effective stabiliser (FP8) in comparison with other prepared pharmaceutical compositions (FP1-FP7) at elevated temperature (40° C., 1 month; FIG. 6) shows that the adsorption of EPO to the vials of FP8 is lower or equal when compared to other formulations. At room temperatures the adsorptions are comparable or better (FIG. 7). An increased adsorption to the vials would decrease the EPO stability, and the entire biological activity would be decreased.

Amino acids have been used as stabilising agent of EPO in the formulations described in prior art. But amino acids do not always exhibit a stabilising effect on EPO. In FIGS. 6 and 7 it is seen that the stability at elevated temperatures (40° C. 1 month) of pharmaceutical compositions FP2 and FP3 comprising glycine is lower than the stability of pharmaceutical preparations FP4, FP5, FP6 and FPB, which do not contain glycine, and is also lower than FP1 which comprises glycine. High EPO stability can be obtained with the use of right combination of different stabilising agents, but their appropriate composition can not be predicted. With the pharmaceutical composition of the present invention it was surprisingly found that PVP stabilised EPO.

The proportion of EPO dimers and related substances of higher molecular mass measured by SEC was compared with diluted solutions of the samples (at a concentration of 2%). The results of limit assay are presented in Table 1 below:

TABLE 1

| | The estimation of EPO dimer proportions | |
|---|---|---|
| Sample | 40° C. 1 month | 25° C. 10 weeks |
| FP1 (2000 IU/ml) | * | * |
| FP1 (10000 IU/ml) | * | * |
| FP2 (2000 IU/ml) | <2% | <2% |
| FP2 (10000 IU/ml) | >2% | <2% |
| FP3 (2000 IU/ml) | >2% | <2% |
| FP3 (10000 IU/ml) | >2% | <2% |
| FP4 (2000 IU/ml) | <2% | <2% |
| FP4 (10000 IU/ml) | <2% | <2% |
| FP5 (2000 IU/ml) | ** | ** |
| FP5 (10000 IU/ml) | (>2%) ** | ** |
| FP6 (2000 IU/ml) | <2% | <2% |
| FP6 (10000 IU/ml) | >2% | <2% |
| FP7 (2000 IU/ml) | <2% | <2% |
| FP7 (10000 IU/ml) | <2% | <2% |
| FP8 (2000 IU/ml) | <2% | <2% |
| FP8 (10000 IU/ml) | <2% | <2% |

* denotes that the determination of the proportion of dimers was not possible due to polysorbates from placebo
** denotes that the determination of the proportion of dimers was not possible due to dextran. Small amounts of higher molecular mass related substances were also detected in most samples, but were not included in the presentation.

The in vivo biological activity was measured in the sample FP8 with an EPO content of 10000 IU/ml, stored at 25° C. for 10 weeks or stored in the refrigerator for 4 months.

The results obtained are presented in Table 2 below:

TABLE 2

| Sample | Estimation of biological activity (80-120%) | Conf. limit (64-156%) |
|---|---|---|
| FP8 (25° C., 10 weeks) | 9059 IU/ml (91%) | 69-143% |
| FP8 (HL, 4 months) | 9917 IU/ml (99%) | 76-129% |

The results show that the estimated biological activity is in the demanded range and corresponds the demands of Eur. Ph. The confidential limits are also in the demanded range.

Examples 2 and 3

Compositions of Pharmaceutical Compositions of EPO

The compositions of inventive (pharmaceutical compositions presented in) Examples 2 and 3 are set out in Tables 3 and 4, respectively.

TABLE 3

| Sample | Active ingredient | Inactive ingredient |
|---|---|---|
| FP8 (2000) | 2000 IU EPO | $NaH_2PO_4 \times 2H_2O$ 1.164 mg<br>$Na_2HPO_4 \times 2H_2O$ 2.225 mg<br>NaCl 7.200 mg<br>PVP K12 5.000 mg<br>NaOH for pH adjustment<br>(pH: 7.0-7.1)<br>Water to 1 ml |

TABLE 4

| Sample | Active ingredient | Inactive ingredient |
|---|---|---|
| FP8 (10000) | 10000 IU EPO | $NaH_2PO_4 \times 2H_2O$ 1,164 mg<br>$Na_2HPO_4 \times 2H_2O$ 2,225 mg<br>NaCl 7.200 mg<br>PVP K12 5.000 mg<br>NaOH for pH adjustment pH<br>(pH: 7.0-7.1)<br>Water to 1 ml |

Quality of Substances:
EPO: quality as demanded by European Pharmacopoeia (Ph Eur. quality), Povidone K12 (poly[1-(2-oxo-1-pyrrolidinyl) ethylen], polyvidone or polyvinylpyrrolidone, PVP) Ph Eur quality, also corresponds to US Pharmacopoeia (USP quality), purchased from BASF, Ludwigshafen, Germany, NaCl, $Na_2HPO_4 x2H_2O$, $NaH_2PO_4 x2H_2O$, NaOH, water for injection: Ph. Eur. quality.

Preparation of Pharmaceutical Compositions Which Comprise EPO

Preparation of placebo solution with PVP K12: buffer ($Na_2HPO_4 x2H_2O$, $NaH_2PO_4 x2H_2O$), NaCl and stabiliser PVP K12 were dissolved in water for injection at room temperature by mixing on the magnetic stirrer. pH was then adjusted with 1M NaOH to 7.0-7.1. A clear and colourless solution was obtained.

Preparation of EPO solution: The calculated volume of the EPO solution (calculations were performed regarding the EPO activity) was added to the placebo solution. Just before this step the same volume of placebo solution was taken out. The solution was stirred by using a magnetic stirrer at low rounds. A clear colorless solution was obtained.

The solutions of pharmaceutical compositions which comprise EPO at both concentrations were then aseptically (air cleanliness level of class 100) sterile filtered through membrane filter with PVDF (Polyvinylidenefluoride) membrane, pore size 0.2 μm. 0.8 ml of the filtered solutions were filled in 2 ml vials (vials from the colourless tubular glass hydrolytic type I) washed and sterilised, and closed with elastic closures from brombutyl rubber and, sealed with aluminium caps.

The invention claimed is:
1. A stable pharmaceutical composition of erythropoietin (EPO), which comprises:
  a. a therapeutically effective amount of EPO,
  b. a pharmaceutically acceptable pH buffering system,
  c. polyvinylpyrrolidone (PVP),
  d. optionally, an isotonifying agent,
  e. optionally, one or more pharmaceutically acceptable excipient(s) selected from the group consisting of polyols, hydroxypropylcellulose, methylcellulose, macrogol esters and ethers, glycol and glycerol esters, and amino acids, and
  f. optionally, a poloxamer as an additional stabilizer
  wherein the polyvinylpyrrolidone (PVP) and the optional poloxamer are the sole stabilizers for the stabilization of the erythropoietin (EPO) and wherein the composition is free of serum proteins, other than EPO, derived from human and/or animal origin.
2. The composition of claim 1, wherein the composition is aqueous.
3. The composition of claim 1, wherein the pharmaceutical quantity of EPO is formulated to provide a quantity per dose in the range of about 500 to about 100000 IU EPO.
4. The composition of claim 3, wherein the pharmaceutical quantity is formulated to provide a quantity per dose selected form the group consisting of about 1000 IU, about 2000 IU, about 3000 IU, about 4000 IU, about 10000 IU, about 20000 IU, about 25000 IU and about 40000 IU.

5. The composition of claim 1, wherein the pH buffering system provides a pH range from about 6 to about 8.

6. The composition of claim 5, wherein the pH buffering system provides a pH range from about 6.8 to about 7.5.

7. The composition of claim 5, wherein the pH buffering system provides a pH of about 7.0.

8. The composition of claim 1, wherein the pH buffering system is phosphate buffer.

9. The composition of claim 1, wherein PVP is comprised in a range of about 0.01% to about 1%.

10. The composition of claim 9, wherein PVP is comprised in a range of about 0.1% to about 1%.

11. The composition of claim 9, wherein the concentration of PVP is about 0.5%.

12. The composition of claim 1, wherein said PVP has a K value in a range from K12 to K18.

13. The composition of claim 1, wherein said isotonifying agent is selected from the group consisting of inorganic salts.

14. The composition of claim 13, wherein said isotonifying agent is NaCl.

15. A stable pharmaceutical composition of erythropoietin (EPO), which comprises:
  a. a therapeutically effective amount of EPO,
  b. a pharmaceutically acceptable pH buffering system,
  c. an EPO stabilizer which comprises polyvinylpyrrolidone (PVP) and optionally a poloxamer,
  d. optionally, an isotonifying agent, and
  e. optionally, one or more pharmaceutically acceptable excipient(s) selected from the group consisting of polyols, hydroxypropylcellulose, methylcellulose, macrogol esters and ethers, glycol and glycerol esters, and amino acids wherein the polyvinylpyrrolidone (PVP) and the optional poloxamer are the sole stabilizers for the stabilization of the erythropoietin (EPO) and wherein the composition is which is free of serum proteins, other than EPO, derived from human and/or animal origin.

16. A stable aqueous solution of erythropoietin (EPO) comprising:
  erythropoietin (EPO), and
  polyvinylpyrrolidone (PVP),
  wherein the polyvinylpyrrolidone (PVP) is the sole stabilizer for the stabilization of the erythropoietin (EPO) and wherein the composition is which is free of serum proteins, other than EPO, derived from human and/or animal origin.

* * * * *